(12) United States Patent
Wilk

(10) Patent No.: US 6,409,684 B1
(45) Date of Patent: Jun. 25, 2002

(54) MEDICAL DIAGNOSTIC DEVICE WITH MULTIPLE SENSORS ON A FLEXIBLE SUBSTRATE AND ASSOCIATED METHODOLOGY

(76) Inventor: Peter J. Wilk, 185 W. End Ave.-Unit 22M, New York, NY (US) 10023

(*) Notice: Subject to any disclaimer, the term of this patent is extended or adjusted under 35 U.S.C. 154(b) by 0 days.

(21) Appl. No.: 09/552,102

(22) Filed: Apr. 19, 2000

(51) Int. Cl.⁷ ................................................ A61B 7/00
(52) U.S. Cl. .................... 600/586; 600/484; 600/587
(58) Field of Search ................................ 600/437, 449, 600/453, 454, 455, 456, 457, 458, 459, 481–484, 500, 528, 529, 538, 544, 546, 549, 552, 553, 586, 587, 597; 73/787, 818

(56) References Cited

U.S. PATENT DOCUMENTS

| | | | | |
|---|---|---|---|---|
| 4,771,792 A | * | 9/1988 | Seale | 600/587 |
| 5,415,167 A | * | 5/1995 | Wilk | 600/407 |
| 5,437,278 A | * | 8/1995 | Wilk | 600/425 |
| 5,524,636 A | * | 6/1996 | Sarvazyan et al. | 600/587 |
| 5,666,953 A | * | 9/1997 | Wilk | 600/407 |
| 5,685,307 A | * | 11/1997 | Holland et al. | 600/437 |
| 6,168,568 B1 | * | 1/2001 | Gavriely | 600/529 |
| 6,213,958 B1 | * | 4/2001 | Winder | 600/586 |
| 6,267,733 B1 | * | 7/2001 | Peterson et al. | 600/587 |

* cited by examiner

Primary Examiner—Kevin Shaver
Assistant Examiner—Charles Marmor, II

(74) Attorney, Agent, or Firm—Neil Sudol; Henry Coleman; William Sapone

(57) ABSTRACT

A medical diagnostic device comprises a substrate or carrier, a plurality of acoustoelectric transducers or sensors attached to the substrate or carrier in a pre-established array, a signal processor operatively coupled to the transducers for determining locations of points of origin of acoustic pressure waves generated by internal tissue structures of a patient on whom the substrate or carrier is placed, and a diagnosis computer operatively coupled to the transducers for automatically analyzing signals from the transducers to determine an internal condition of the patient. The device optionally includes a plurality of mechanical probes movably mounted to the substrate or carrier and actuators operatively connected to the probes for inducing movement of the probes, in a direction perpendicular to the substrate or carrier, from nascent or retracted positions to extended positions. The computer is operatively connected to the actuators for varying extension rate of the probes and for inducing a predetermined sequence of actuation of the probes. A plurality of additional sensors may be mounted to the substrate or carrier for measuring a preselected physiological parameter at different locations along a patient's skin surface. The computer is operatively connected to the sensors for analyzing readings from the sensors in accordance with values of the parameter stored in a memory. The additional sensors are preferably, but not exclusively, taken from the group consisting of temperature sensors, electrical skin resistance detectors, Doppler blood flow sensors, electronic blood pressure gauges, muscle tone measurement devices, EEG electrodes, EKG electrodes.

34 Claims, 2 Drawing Sheets

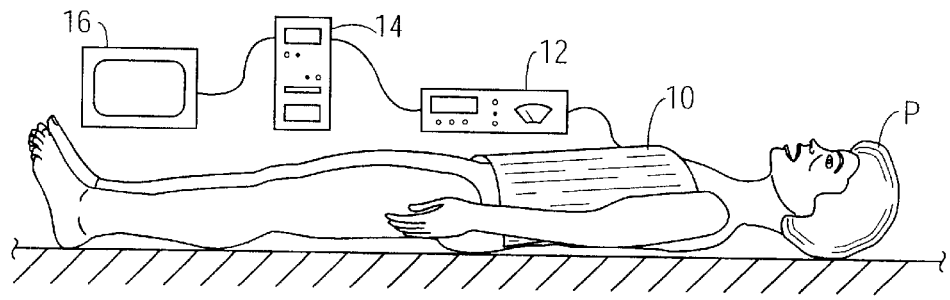
FIG. 1
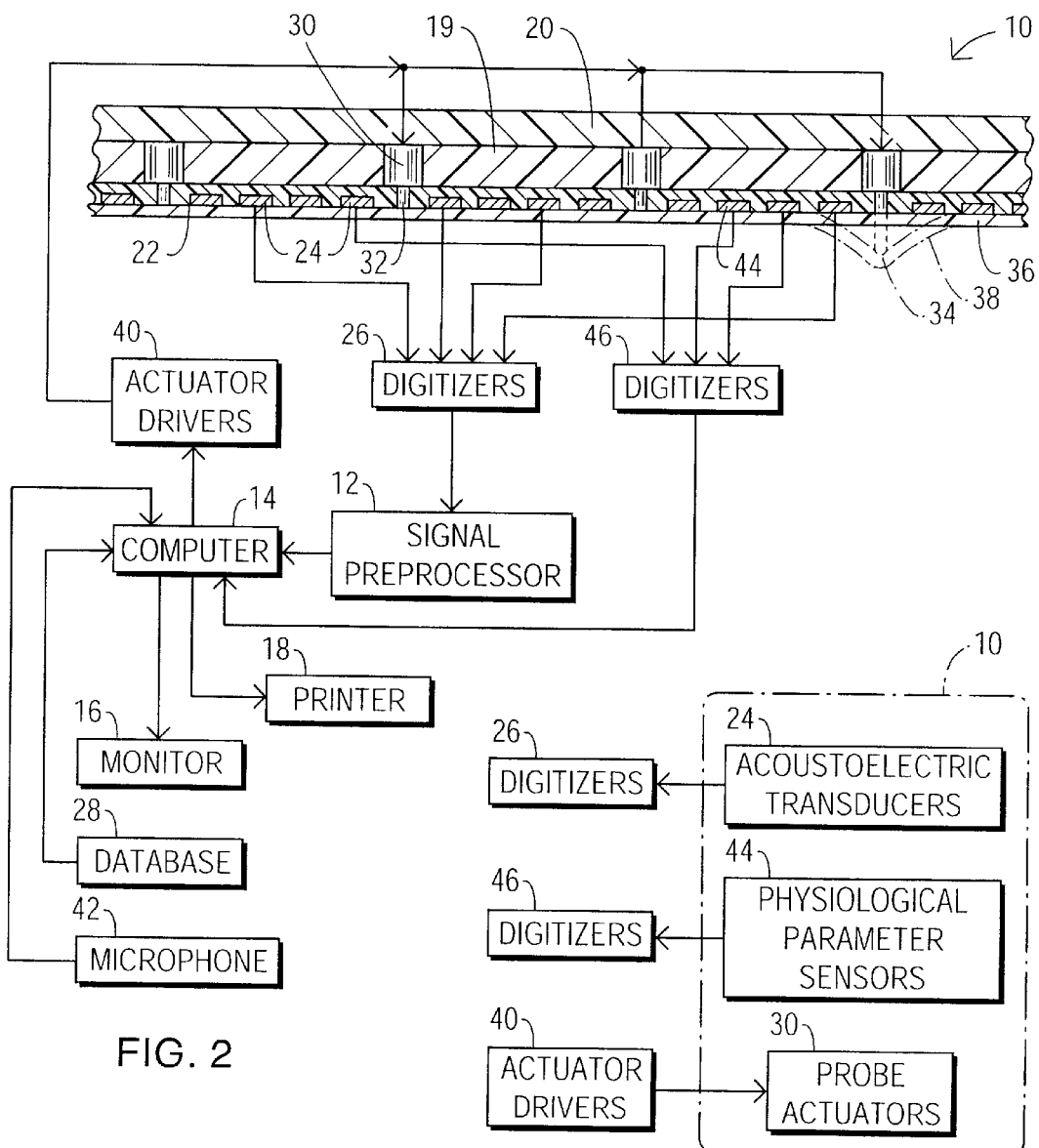
FIG. 2
FIG. 3

MEDICAL DIAGNOSTIC DEVICE WITH MULTIPLE SENSORS ON A FLEXIBLE SUBSTRATE AND ASSOCIATED METHODOLOGY

BACKGROUND OF THE INVENTION

This invention relates to a medical diagnostic device. The invention also relates to an associated medical method.

The traditional practice of medicine entails a close observation and "hand-on" examination of a patient to gather information for performing a diagnosis of the patient's medical condition. The observation includes use of a stethoscope to listen to sounds produced by the internal tissues and organs of the patient. With a stethoscope, an experienced physician listening for sounds in the chest region can detect wheezing and whistling indicating a constriction or narrowing of the bronchial passages. No breath sound or a greatly diminished breathing sound may indicate the presence of a lung tumor. Alternatively, the absence of sound may be due to the filling of the aveoli from pneumonia. A popping sound may be caused by pneumothorax, air not being returned owing to a hole in the lung. In the abdomen, aneurysms and arteriosclerotic narrowing generate characteristic low-amplitude vibrations or pressure waves recognizable by an experienced ear. Abnormalities in heart valve function can be detected by a seasoned medical practitioner.

With the advent of advanced medical diagnostic devices such as CAT scanners, MRI machines, echocardiograms, and EKG equipment, the art of listening with a stethoscope and observing a patient has largely disappeared. Many new doctors are unable to diagnose without expensive test results. Moreover, complex modem testing generally delays the diagnosis of a patient's condition.

OBJECTS OF THE INVENTION

An object of the present invention is to provide a medical diagnostic apparatus and/or an associated medical methodology.

It is another object of the present invention to provide a medical diagnostic apparatus and/or an associated method which facilitates the collection of information of a kind traditionally obtained through a hand-on examination of a patient.

Another, more specific, object of the present invention is to provide a medical diagnostic apparatus which monitors sounds traditionally detected through use of a stethoscope.

A further object of the present invention is to provide such a medical diagnostic apparatus which is easy to use.

An additional object of the present invention is to provide such a medical diagnostic apparatus which facilitates the quick provision of medical diagnoses.

These and other objects of the present invention will be apparent from the drawings and descriptions herein.

SUMMARY OF THE INVENTION

A medical diagnostic device comprises a substrate or carrier, a plurality of acoustoelectric transducers or sensors attached to the substrate or carrier in a pre-established array, and a diagnosis generator operatively coupled to the transducers for automatically analyzing signals from the transducers to determine an internal condition of the patient. Optionally, the device further comprises a signal processor operatively coupled to the transducers for determining locations of points of origin of acoustic pressure waves generated by internal tissue structures of a patient on whom the substrate or carrier is placed.

In accordance with another feature of the present invention, the diagnosis generator is a digital computer. The transducers detect sounds produced by internal tissues of the patient and generate electrical signals encoding the detected sounds. The computer includes a memory storing a multiplicity of digitally encoded sample sounds produced by preselected internal tissues in abnormal conditions and further includes a comparator operatively connected to the memory and the transducers for comparing electrical signals from the transducers with sample sounds stored in the memory.

In accordance with a further feature of the present invention, the device additionally comprises a plurality of mechanical probes movably mounted to the substrate or carrier and actuators operatively connected to the probes for inducing movement of the probes, in a direction perpendicular to the substrate or carrier, from nascent or retracted positions to extended positions. The memory includes or stores sample sounds produced by internal tissues in response to percussive movements made by the probes, while the computer is operatively connected to the actuators for controlling operation thereof. More specifically, the computer includes programming for varying extension rate of the probes and for inducing a predetermined sequence of actuation of the probes.

Pursuant to an additional feature of the present invention, the device further comprises a plurality of additional sensors mounted to the substrate or carrier for measuring a preselected physiological parameter at different locations along a patient's skin surface. In that event, the memory additionally stores patterns of values of the parameter associated with different diagnostic conditions, while the computer is operatively connected to the sensors for analyzing readings from the sensors in accordance with values of the parameter stored in the memory. The additional sensors are preferably, but not exclusively, taken from the group consisting of temperature sensors, electrical skin resistance detectors, Doppler blood flow sensors, electronic blood pressure gauges, muscle tone measurement devices, EEG electrodes, EKG electrodes.

Where the sample sounds are characterized by respective patterns, the comparator is a pattern comparator.

Preferably, the substrate or carrier includes at least one flexible portion so that a first part of the substrate or carrier is disposable at an angle with respect to a second part of the substrate or carrier. More preferably, the substrate or carrier is flexible at multiple locations or even flexible throughout a continuous area so that the substrate or carrier is substantially conformable to a skin surface of a patient.

Another medical diagnostic device comprises, in accordance with a variant of the present invention, a substrate or carrier, a plurality of mechanical probes movably mounted to the substrate or carrier, and actuators operatively connected to the probes for inducing movement of the probes, in a direction perpendicular to the substrate or carrier, from nascent or retracted positions to extended positions. Sensors may be attached to the substrate or carrier for detecting a response of internal tissues of a patient to action of the probes after placement of the substrate or carrier in operative contact with the patient and movement of at least one of the probes by the actuators. A diagnosis generator may be operatively coupled to the sensors for automatically analyzing signals from the sensors to determine an internal condition of the patient.

Yet another medical diagnostic device comprises, in accordance with a variant of the present invention, a substrate or carrier, a plurality of sensors mounted to the substrate or carrier for measuring a preselected physiological parameter at different locations along a patient's skin surface, a memory storing patterns of values of the parameter associated with different diagnostic conditions, and a computer operatively connected to the sensors and the memory for analyzing readings from the sensors in accordance with values of the parameter stored in the memory.

A medical diagnostic apparatus in accordance with the present invention not only facilitates the collection of information of a kind traditionally obtained through a hand-on examination of a patient, but also facilitates the diagnosis of medical conditions based on the collected information. It is contemplated that the diagnosis is implemented automatically. Inasmuch as the knowledge and capabilities of experienced hands-on practitioners may be used in constructing the database and programming the diagnostic computer, the present invention envisions a substantial improvement in medical care. The knowledge and talents of past practitioners can be effectively stored for the use of future generations.

A medical diagnostic method comprises, in accordance with the present invention, placing a multiplicity of acoustoelectric transducers in effective pressure-wave-transmitting contact with a patient and automatically analyzing electrical signals from the transducers to automatically determine an internal condition of the patient. The automatic analysis of the electrical signals preferably includes operating a digital computer. Where the transducers detect sounds or audible-range pressure waves produced by internal tissues of the patient and generate electrical signals encoding the detected sounds, the operating of the computer includes processing the electrical signals and comparing the processed signals with sample sounds stored in a memory.

In accordance with an additional feature of the present invention, the method further comprises placing a plurality of probes adjacent to the patient and operating actuators to move selected ones of the probes from nascent or retracted positions to extended positions pushing against the patient. The computer is then operated to compare sample sounds in the memory with sounds produced by internal tissues in response to the movements made by the probes.

A medical diagnostic method comprises, pursuant to another feature of the present invention, placing, in effective contact with a patient at different locations along a patient's skin surface, a plurality of sensors for measuring a preselected physiological parameter. Patterns of values of the parameter associated with different diagnostic conditions are stored in a memory. A computer is operated to analyze readings from the sensors in accordance with values of the parameter stored in the memory.

BRIEF DESCRIPTION OF THE DRAWINGS

FIG. 1 is a schematic elevational view of a medical diagnostic apparatus for monitoring and analyzing patterns of pressure wave (sounds) produced by activity internal to a patient, in accordance with the present invention.

FIG. 2 is partially a block diagram and partially a cross-sectional view of a flexible transducer carrier shown in FIG. 1.

FIG. 3 is a block diagram showing transducers in the flexible carrier of FIGS. 1 and 2.

DESCRIPTION OF THE PREFERRED EMBODIMENTS

Figure 4:
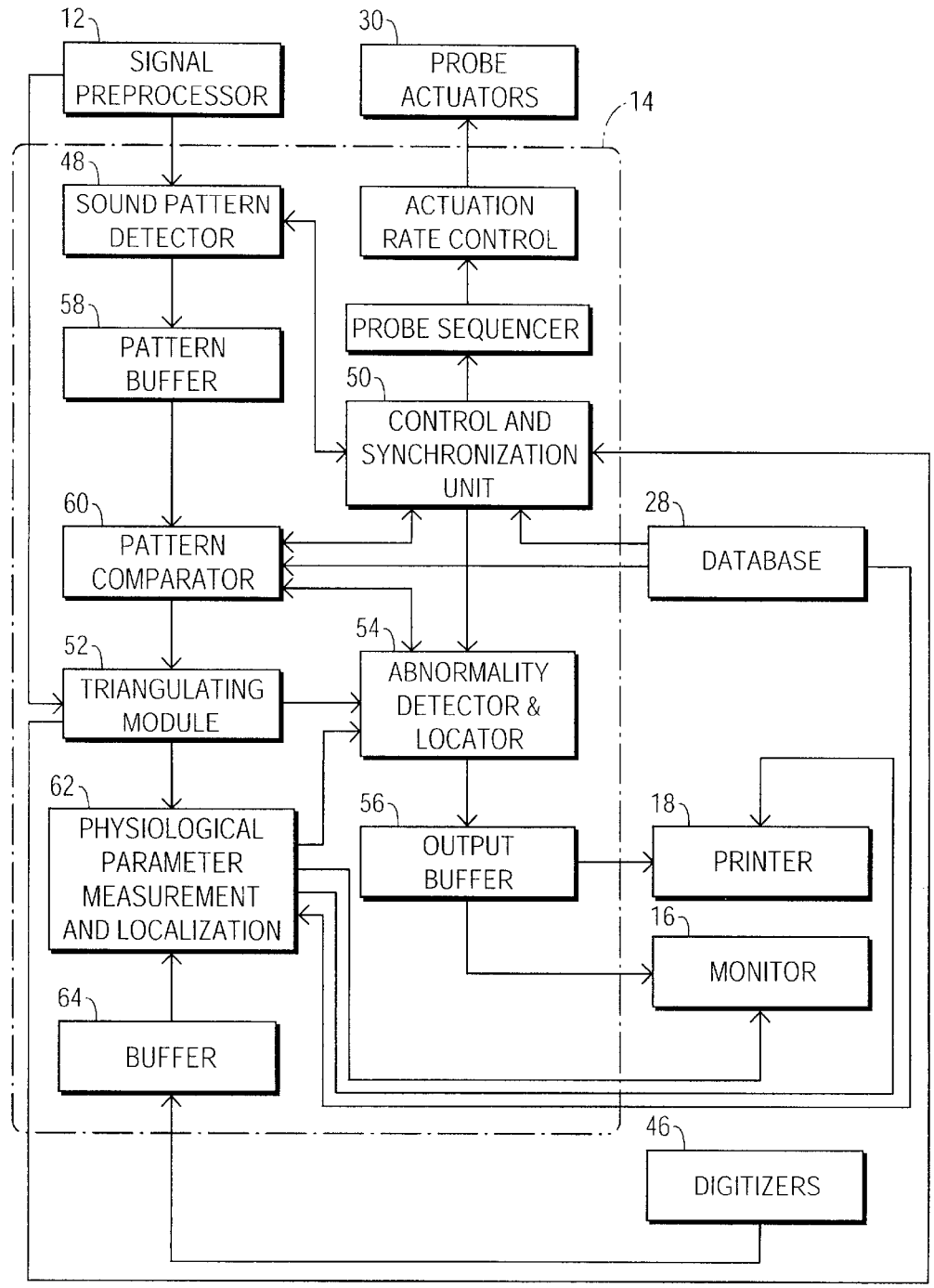
FIG. 4 is a block diagram depicting components of a computer shown in FIGS. 1 and 2.

As illustrated in FIG. 1, a medical diagnostic apparatus comprises a flexible carrier member 10 conformable to a portion of a patient P, for example, the chest region or the abdominal region. Carrier member 10 is operatively connected to a signal preprocessor 12 which in turn is connected to a computer 14. Computer 14 generates a diagnosis of the patient P which may be communicated to an operator via a monitor 16 or a printer 18 (FIG. 2).

Carrier member 10 includes a base layer 19 of a strong flexible material such as KEVLAR™ or TEFLON™ strands embedded in a polyethylene or polypropylene matrix. On one side of base layer 19 is a weighted layer 20 including a heavy material such as ceramic or metallic particles embedded in a polymeric matrix. Accordingly, weighted layer 20 is also flexible, enabling carrier member 10 to conform to a person's chest surfaces. Carrier member 10 further includes a third layer 22 of a polymeric material which is disposed on a side of base layer 18 opposite weighted layer 20 and in which are embedded a plurality of acoustoelectric transducers 24 (see FIG. 3) made of a piezoelectric material. Transducers 24 are generally distributed in a predetermined array substantially throughout the extent of carrier member 10.

Transducers 24 sense pressure waves generally having frequencies within an audible range. Thus, transducers 24 sense vibrations or pressure waves which would be detectible by a sufficiently experienced physician using a stethoscope. Analog electrical signals are generated by transducers 24 in response to incoming pressure waves and are transmitted to a bank of digitizers 26 shown in FIGS. 2–4. Digital signals consequently produced at outputs of the digitizers 26 are fed to signal preprocessor 12 which serves to process incoming bit streams, e.g., using Fourier analysis, into higher order data sequences. Computer 14 analyzes the higher order data sequences to determine patterns of sound and compares detected patterns with previously identified sound patterns stored in a bulk memory or database 28. The previously stored sound patterns are identified at least in part by physical or physiological conditions known to give rise to the respective sound patterns. Thus, by detecting a match, within pre-established tolerances, between a sound pattern identified from a patient and a previously measured sound pattern, computer 14 arrives at a diagnosis.

As shown in FIGS. 2 and 3, carrier member 10 also contains a plurality of mechanical actuators 30 operatively connected to respective movable probes or plungers 32 for shifting the probes from withdrawn or retracted neutral positions to extended testing positions 34. Probes 32, as well as transducers 24 are protected by a flexible cover layer 36 made of a resilient polymeric material and attached to a side of layer 22 opposite base layer 19. Cover layer 36 flexes and stretches, as shown at 38, during an extension of a probe 32.

Actuators 30 may be hydraulic, pneumatic, or electromagnetic and are energized by respective actuator drivers 40 under the control of computer 14. Probes 32 perform a testing function traditionally performed by the finger of a physician. Probes 32 are thus used to prod a patient in predetermined locations and with a force, depth and speed known to elicit certain responses when the patient is suffering from given physical and physiological disfunctions. The responses may be internally generated pressure waves detectible by transducers 24. Alternatively, the responses may be vocalizations of a patient indicating the existence of pain. Such vocalizations are monitored by a microphone 42 (FIG. 2) which is connected at an output to computer 14 for enabling the computer to associate prodding or probing of the patient with the patient's vocal responses. Database 28 may be consulted by computer 14 to determine a diagnosis in response to the patient's vocalizations. In addition, database 28 may provide computer 14 with information as to which points on a patient to apply mechanical pressure and the mode of application and release of the pressure (e.g., slow probe extension and rapid release).

As further illustrated in FIGS. 2 and 3, carrier member 10 and particularly layer 22 thereof may also contain additional sensors 44 embedded in a predetermined array throughout the extent of carrier member 10 for measuring one or more physiological parameters at different locations along the patient's skin surface. In that event, memory or database 28 additionally stores ranges and patterns of values of the parameter(s) associated with different diagnostic conditions, while computer 14 is operatively connected to sensors 44 for analyzing readings from the sensors in accordance with values of the parameter(s) stored in the memory or database. Physiological parameters which may be measured by sensors 44 include temperature, electrical skin resistance, blood flow, electronic blood pressure, muscle tone, brain waves and cardiac action potentials. Sensors 44 are thus taken from the group consisting of temperature sensors, electrical skin resistance detectors, Doppler blood flow sensors, electronic blood pressure gauges, muscle tone measurement devices, EEG electrodes, EKG electrodes.

Sensors 44 are connected at their outputs to a set of digitizers 46 which convert analog output signals of the sensors to digital bit streams fed to computer 14. As described in U.S. Pat. No. 5,437,278, it may be necessary for computer 14 to correlate input from a plurality of sensors 44 of the same kind in order to measure a particular physiological function. For example, to obtain an EEG, EKG, or EMG measurement, the electric potential at different points on the patient's body must be sensed essentially simultaneously over a minimal period. A preprocessor (not separately shown) may be used to break these variables down into one or more pre-established parameters, e.g., a frequency packet. The measured values of the pre-established parameters are then compared with parameter ranges stored in memory or database 28 for the type of parameter and the kind of patient, as characterized by sex, age, weight, etc. If the measured values of the pre-established parameters fall within expected ranges, as stored in memory 28, then computer 14 communicates a "normalcy" finding via monitor 16 and/or printer 18. If, on the contrary, the measured values of one or more parameters fall outside the normal ranges, then a diagnosis of a possible medical condition is printed out.

The physiological parameters measured by computer 14 in response to the output signals of sensors 44 may be analyzed together with pressure waves monitored by transducers 24, preprocessor 12 and computer 14 to derive a diagnosis based on multiple inputs. The automatic confirmation inherent in such a diagnostic process results in a greater reliability, as well as a capability of diagnosing an increased number and complexity of conditions. Thus, EKG measurements effectuated with sensors 44 in the form of capacitative electrodes as disclosed in U.S. Pat. No. 5,257,631 may be analyzed together with acoustic patterns detected via transducers 24 to make an automatic diagnosis of mitral stenosis or aortic valve malfunction. Other kinds of cardiac conditions also give rise to both EKG artifacts and acoustically detectible irregularities. With reference to the lungs, localized infections can be detected from breathing sounds taken in conjunction with temperature and blood flow measurements over the chest cavity. In the abdomen, aneurysms produce characteristic flow sounds as well as variations in flow rate detectible through Doppler measurements.

FIG. 4 depicts selected functional modules of computer 14. These modules are preferably implemented by generic digital processing circuits modified by programming to accomplish the intended functions. However, the various functional modules may be alternatively implemented in the form of hard wired, dedicated circuits designed exclusively for performing the respective tasks.

Computer 14 includes a sound pattern detector 48 receiving the higher-order data signals from preprocessor 12. In a controlled iterative process, pattern detector 48 organizes and reorganizes the incoming data stream to detect pressure wave patterns that correspond more or less to recognized sounds. With respect to the activity of the lungs, possible sounds include normal air flow sounds, as well as abnormal wheezing, whistling, popping, and silence. With respect to the heart, possible sounds include the normal heart beat, as well as various arrhythmias, tachycardia, and the acoustic artifacts of impaired valve function. Pattern detector 48 functions in part to filter out variations in frequency owing to dimensional variations in organic structures giving rise to the various sounds. Thus, an aneurysm will be detectible essentially regardless of its size.

Sound pattern detector 48 may also be connected to microphone 42 (FIG. 2) for using voice-recognition techniques to determine that the individual patient has uttered a sound and for characterizing that sound as to intensity, suddenness or sharpness, depth, etc. These detected uttered sounds are correlated with operation of probe actuators 30, under the control of a control and synchronization unit 50. More specifically, control and synchronization unit 50 accesses database 28 to determine which probe actuators 30 are to be actuated, i.e., a sequence of actuation, as well as a rate of extension, a degree of extension, and a rate of release for each probe 32. The particular probe actuation parameters found in database 28 by control and synchronization unit 50 depend in part on the position of carrier member 10 relative to patient P: different probes 32 are actuated if the carrier member is shifted relative to the patient. The location of carrier member 10 on patient P is determined by a triangulating module 52, the operation of which is discussed hereinafter.

Control and synchronization unit 50 determines from pattern detector 48 whether patient P has vocally reacted to a prodding by a particular probe 32. A reaction of pain, for instance, to a probe extension (or retraction) in a particular location may be generally indicative of an internal organic or physiological abnormality. Control and synchronization unit 50 communicates to an abnormality detector and locator 54 diagnostic data gleaned from detected reactions of a patient to extensions (or retractions) of probes 32. Detector and locator 54 is connected to an output buffer 56 in turn connected to monitor 16 and printer 18 for communicating diagnostic results to an operator.

Pattern detector 48 is connected at an output to a pattern buffer 58 which retains the detected patterns for a sufficient period of time to allow comparison of the detected patterns by a comparator 60 with previously stored acoustic patterns in database 28. Comparator 60 thus uses acoustic pattern data to identify possible organic deformations and physiological malfunctions. Examples of possible automatically performed diagnoses are alluded to hereinabove and include (a) a constriction or narrowing of the bronchial passages signaled by wheezing and whistling in the chest region, (b) a lung tumor or pneumonia indicated by an absence of breath sound or a greatly diminished breathing sound, (c) pneumothorax evidenced by a popping sound, (d) a hole in a lung indicated by air not being returned, (e) mitral stenosis correlated with certain kinds of aortic valve movement, (f) aneurysms and arteriosclerotic narrowing corresponding to characteristic low-amplitude vibrations or pressure waves, etc.

Pattern comparator 60 is connected at an output to triangulating module 52 which may also be connected directly to signal preprocessor 12. Triangulating module 52 utilizes selected sounds identified by pattern comparator 60 to determine which data stream bytes from preprocessor 12 originate in which organs of the patient. The relative intensities of the sounds are used in a triangulation algorithm to derive position information. Thus, triangulating module 52 uses detected sounds made by known organs having generally known locations in a patient P to determine the position and orientation of carrier member 10 (and particularly transducers 24) relative to the patient's internal organs.

Pattern comparator 60 and triangulating module 52 are connected to abnormality detector and locator module 54. Module 54 correlates the pattern comparison results from comparator 60 with position information from triangulating module 52 to provide an operator with a diagnosis including an identification of the part(s) of the patient where an abnormal condition has been detected. Thus, the absence of breath sound only in a particular lobe of a lung indicates that a tumor may be located in that lobe. In contrast, the absence of breathing sound in several lobes may more likely be caused by pneumonia.

A diagnosis essentially made by comparator 60 may be confirmed or refined by abnormality detector and locator module 54. To that end, module 54 receives ancillary physiological data which is gathered by sensors 44, converted into digital format by digitizers 46, and analyzed by a measurement and localization module 62. Digitized physiological data from sensors 44 is temporarily stored by a bank of buffer registers 64 to facilitate sampling thereof by measurement and localization module 62. Module 62 also receives position information from triangulating module 52 to facilitate the correlation of physiological data from sensors 44 with previously measured parametric ranges. Thus, module 62 can determine skin temperatures, electrical skin resistance values, blood flow rates, and muscle tone at different ascertainable locations on the patient P and can correlate electrical potential measurements from a plurality of distributed electrical potential detectors or sensors 44 with each other and with locations on the patient to measure, for instance, EKG or cardiac action potentials. Module 62 accesses database 28 to make comparisons and determine correlations.

Although the invention has been described in terms of particular embodiments and applications, one of ordinary skill in the art, in light of this teaching, can generate additional embodiments and modifications without departing from the spirit of or exceeding the scope of the claimed invention. It is to be noted, for example, that transducers 24 may sense incoming pressure waves in an ultrasonic range as well as in an acoustic range. In that event, carrier member 10 may be provided with ultrasonic electroacoustic transducers for generating ultrasonic pressure waves in a patient.

Triangulating module 52 may use additional or alternative techniques for localizing sound sources and deriving position data. Such alternative techniques include the manual placement of reference position markers exemplarily in the form of piezoelectric acoustic wave generators (not shown) at predetermined locations on a patient, such as the sternum. Through transducers 24 and signal preprocessor 12, triangulating module 52 receives reference or beacon signals "broadcast" by the position markers and deduces the position and orientation of carrier member 10 relative to patient P.

Probes 32 or actuators 30 may be provided with feedback sensors (not shown) for detecting the degree of resistance to penetration by organic tissues by probes 32. This feedback may be monitored and analyzed for diagnostic purposes. Again, a comparison may be made with prerecorded mechanical resistance measures to automatically ascertain the degree of internal tissues hardness or, alternatively, resiliency and to automatically perform a diagnosis, possibly in concert with other detected indications as described herein.

Accordingly, it is to be understood that the drawings and descriptions herein are proffered by way of example to facilitate comprehension of the invention and should not be construed to limit the scope thereof.

What is claimed is:

1. A medical diagnostic device comprising:
   a substrate or carrier;
   a plurality of acoustoelectric transducers attached to said substrate or carrier in a pre-established array; and
   diagnosis means operatively coupled to said transducers for automatically analyzing signals from said tranducers to automatically determine an internal condition of a patient, further comprising;
   a plurality of mechanical probes movably mounted to said substrate or carrier; and
   actuators operatively connected to said probes for inducing movement of said probes, in a direction substantially perpendicular to said substrate or carrier, from nascent or retracted positions to extended positions.

2. The device defined in claim 1 wherein said diagnosis means is a digital computer.

3. The device defined in claim 2 wherein said transducers detect sounds or audible-range pressure waves produced by internal tissues of the patient and generate electrical signals encoding the detected sounds, said computer including:
   a memory storing a multiplicity of digitally encoded sample sounds produced by preselected internal tissues in abnormal conditions; and
   a comparator operatively connected to said memory and said transducers for comparing electrical signals from said transducers with sample sounds stored in said memory.

4. The device defined in claim 2 wherein said memory includes sample sounds produced by internal tissues in response to percussive movements made by said probes.

5. The device defined in claim 3 wherein said sample sounds are characterized by respective patterns, said comparator being a pattern comparator.

6. The device defined in claim 4 wherein said computer is operatively connected to said actuators for controlling operation thereof.

7. The device defined in claim 4, further comprising a plurality of additional sensors mounted to said substrate or carrier for measuring a preselected physiological parameter at different locations along a patient's skin surface, said memory additionally storing patterns of values of said parameter associated with different diagnostic conditions, said computer being operatively connected to said sensors for analyzing readings from said sensors in accordance with values of said parameter stored in said memory.

8. The device defined in claim 6 wherein said computer includes programming for varying extension rate of said probes.

9. The device defined in claim 6 wherein said computer includes programming for inducing a predetermined sequence of actuation of said probes.

10. The device defined in claim 7 wherein said additional sensors are taken from the group consisting of temperature sensors, electrical skin resistance detectors, Doppler blood flow sensors, electronic blood pressure gauges, muscle tone measurement devices, EEG electrodes, and EKG electrodes.

11. The device defined in claim 1 wherein said substrate or carrier includes at least one flexible portion so that a first part of said substrate or carrier is disposable at an angle with respect to a second part of said substrate or carrier.

12. The device defined in claim 11 wherein said substrate or carrier is flexible at multiple locations so that said substrate or carrier is substantially conformable to a skin surface of a patient.

13. The device defined in claim 1 wherein said diagnosis means includes a memory storing sample sounds produced by internal tissues in response to percussive movements made by said probes, said diagnosis means being operatively connected to said actuators for controlling operation thereof.

14. The device defined in claim 13 wherein said diagnosis means includes programming for varying extension rate of said probes.

15. The device defined in claim 13 wherein said diagnosis means includes programming for inducing a predetermined sequence of actuation of said probes.

16. The device defined in claim 1, further comprising a plurality of additional sensors mounted to said substrate or carrier for measuring a preselected physiological parameter at different locations along a patient's skin surface, said diagnosis means including a memory storing patterns of values of said parameter associated with different diagnostic conditions, said diagnosis means being operatively connected to said sensors for analyzing readings from said sensors in accordance with values of said parameter stored in said memory.

17. The device defined in claim 16 wherein said additional sensors are taken from the group consisting of temperature sensors, electrical skin resistance detectors, Doppler blood flow sensors, electronic blood pressure gauges, muscle tone measurement devices, EEG electrodes, and EKG electrodes.

18. The device defined in claim 1 wherein said transducers detect sounds or audible-range pressure waves produced by internal tissues of the patient and generate electrical signals encoding the detected sounds, said diagnosis means including:
   a memory storing a multiplicity of sample sounds produced by preselected internal tissues in abnormal conditions; and
   a comparator operatively connected to said memory and said transducers for comparing electrical signals from said transducers with sample sounds stored in said memory.

19. The device defined in claim 1, further comprising signal processing means operatively coupled to said transducers for determining locations of points of origin of acoustic or audible-range pressure waves generated by internal tissue structures of a patient on whom said substrate or carrier is placed.

20. A medical diagnostic device comprising:
   a substrate or carrier;
   a plurality of mechanical probes movably mounted to said substrate or carrier;
   actuators operatively connected to said probes for inducing movement of said probes, in a direction perpendicular to said substrate or carrier, from nascent or retracted positions to extended positions;
   sensors attached to said substrate or carrier for detecting a response of internal tissues of a patient to action of said probes after placement of said substrate or carrier in operative contact with the patient and movement of at least one of said probes by said actuators; and
   diagnosis means operatively coupled to said sensors for automatically analyzing signals from said sensors to determine an internal condition of the patient.

21. The device defined in claim 20 wherein said diagnosis means is a digital computer.

22. The device defined in claim 21 wherein said sensors detect sounds or audible-range pressure waves produced by internal tissues of the patient and generate electrical signals encoding the detected sounds, said computer including:
   a memory storing a multiplicity of digitally encoded sample sounds produced by preselected internal tissues in abnormal conditions; and
   a comparator operatively connected to said memory and said sensors for comparing electrical signals from said sensors with sample sounds stored in said memory.

23. The device defined in claim 22 wherein said computer is operatively connected to said actuators for controlling operation thereof.

24. The device defined in claim 23 wherein said computer includes programming for varying extension rate of said probes.

25. The device defined in claim 23 wherein said computer includes programming for inducing a predetermined sequence of actuation of said probes.

26. The device defined in claim 20, further comprising a plurality of additional sensors mounted to said substrate or carrier for measuring a preselected physiological parameter at different locations along a patient's skin surface, said memory additionally storing patterns of values of said parameter associated with different diagnostic conditions, said computer being operatively connected to said sensors for analyzing readings from said sensors in accordance with values of said parameter stored in said memory.

27. The device defined in claim 26 wherein said additional sensors are taken from the group consisting of temperature sensors, electrical skin resistance detectors, Doppler blood flow sensors, electronic blood pressure gauges, muscle tone measurement devices, EEG electrodes, and EKG electrodes.

28. The device defined in claim 20 wherein said substrate or carrier includes at least one flexible portion so that a first part of said substrate or carrier is disposable at an angle with respect to a second part of said substrate or carrier.

29. The device defined in claim 28 wherein said substrate or carrier is flexible at multiple locations so that said substrate or carrier is substantially conformable to a skin surface of a patient.

30. A medical diagnostic method comprising:
   placing a multiplicity of acoustoelectric transducers in effective pressure-wave-transmitting contact with a patient; and
   automatically analyzing electrical signals from said transducers to automatically determine an internal condition of the patient,
   wherein the automatic analysis of said electrical signals includes operating a digital computer and wherein said transducers detect sounds or audible-range pressure waves produced by internal tissues of the patient and generate electrical signals encoding the detected sounds, the operating of said computer including processing said electrical signals and comparing the processed signals with sample sounds stored in a memory, further comprising:

placing a plurality of probes adjacent to the patient and operating actuators to move selected ones of said probes from nascent or retracted positions to extended positions pushing against the patient; and operating said computer to compare sample sounds in said memory with sounds produced by internal tissues in response to the movements made by said probes.

31. A medical diagnostic method comprising:

disposing a plurality of movable mechanical probes adjacent to a patient;

selectively activating actuators operatively connected to said probes for inducing movement of selected ones of said probes from nascent or retracted positions to extended positions pushing against the patient;

automatically detecting a response of internal tissues of a patient to action of said probes; and automatically analyzing the response of said internal tissues to determine an internal condition of the patient.

32. The method defined in claim 31 wherein the automatic analyzing of the response of said internal tissues includes operating a digital computer.

33. The method defined in claim 32 wherein the response of said internal tissues includes sounds or audible-range pressure waves produced by said internal tissues, the operating of said computer including:

storing a multiplicity of digitally encoded sample sounds produced by preselected internal tissues in abnormal conditions; and comparing electrical signals encoding the response of said internal tissues with stored sample sounds.

34. The method defined in claim 33, further comprising operating said computer to control operation of said actuators.

* * * * *